(12) United States Patent
Arnholt

(10) Patent No.: US 8,639,356 B2
(45) Date of Patent: Jan. 28, 2014

(54) LEAD ASSEMBLY AND RELATED METHODS

(75) Inventor: Devon N. Arnholt, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 620 days.

(21) Appl. No.: 12/437,519

(22) Filed: May 7, 2009

(65) Prior Publication Data

US 2009/0281607 A1 Nov. 12, 2009

Related U.S. Application Data

(60) Provisional application No. 61/051,261, filed on May 7, 2008.

(51) Int. Cl.
*A61N 1/00* (2006.01)

(52) U.S. Cl.
USPC .......................................... 607/122

(58) Field of Classification Search
USPC .................. 607/122, 115, 116, 119
See application file for complete search history.

(56) References Cited

U.S. PATENT DOCUMENTS

| 5,433,742 | A | | 7/1995 | Willis | |
|---|---|---|---|---|---|
| 5,476,589 | A | | 12/1995 | Bacino | |
| 5,609,622 | A | | 3/1997 | Soukup et al. | |
| 5,789,720 | A | | 8/1998 | LaGally et al. | |
| 5,803,928 | A | * | 9/1998 | Tockman et al. | 607/122 |
| 5,861,023 | A | | 1/1999 | Vachon | |
| 5,964,793 | A | | 10/1999 | Rutten et al. | |
| 6,148,237 | A | * | 11/2000 | Das | 607/122 |
| 6,493,591 | B1 | * | 12/2002 | Stokes | 607/127 |
| 6,505,081 | B1 | | 1/2003 | Das | |
| 6,533,779 | B2 | | 3/2003 | Kinsella et al. | |
| 6,968,237 | B2 | | 11/2005 | Doan et al. | |
| 7,013,182 | B1 | | 3/2006 | Krishnan | |
| 7,020,529 | B2 | * | 3/2006 | Krall et al. | 607/122 |
| 7,079,902 | B2 | | 7/2006 | Soukup et al. | |
| 7,212,868 | B2 | * | 5/2007 | McAuliffe | 607/116 |
| 7,313,445 | B2 | * | 12/2007 | McVenes et al. | 607/127 |
| 2002/0147486 | A1 | | 10/2002 | Soukup et al. | |
| 2004/0167595 | A1 | | 8/2004 | Tuominen | |
| 2005/0228469 | A1 | | 10/2005 | Zarembo et al. | |
| 2006/0241734 | A1 | | 10/2006 | Marshall et al. | |
| 2006/0282144 | A1 | | 12/2006 | Knapp et al. | |
| 2007/0038278 | A1 | | 2/2007 | Zarembo | |
| 2008/0183261 | A1 | * | 7/2008 | Hammill et al. | 607/119 |
| 2008/0294158 | A1 | | 11/2008 | Pappone et al. | |
| 2009/0112300 | A1 | | 4/2009 | Horn-Wyffels | |
| 2009/0287285 | A1 | | 11/2009 | Lynn | |
| 2009/0287286 | A1 | | 11/2009 | Lynn | |
| 2009/0306753 | A1 | | 12/2009 | Lynn et al. | |
| 2009/0319014 | A1 | | 12/2009 | Muecke et al. | |

OTHER PUBLICATIONS

International Search Report and Written Opinion Issued in PCT/US2009/002859, mailed Dec. 2, 2009, 17 pages.

* cited by examiner

*Primary Examiner* — Christopher D Koharski
*Assistant Examiner* — Philip Edwards
(74) *Attorney, Agent, or Firm* — Faegre Baker Daniels LLP

(57) ABSTRACT

Defibrillator lead designs and methods for manufacturing a lead having attachment between a fibrosis-limiting material covering, a shocking coil electrode, and an implantable lead body are disclosed herein. An electrode coil fitting is disposed within the shocking coil electrode. In an option, the fibrosis limiting material extends past the ends of the electrode coil, and is wrapped between the coil electrode and the electrode coil member.

12 Claims, 11 Drawing Sheets

LEAD ASSEMBLY AND RELATED METHODS

RELATED APPLICATIONS

This application claims the benefit under 35 U.S.C. 119(e) of U.S. Provisional Patent Application Ser. No. 61/051,261, filed on May 7, 2008, which is incorporated herein by reference in it entirety.

TECHNICAL FIELD

This document pertains generally to implantable defibrillator leads with fibrosis-limiting material.

BACKGROUND

Cardiac and other defibrillation systems typically include an implantable medical device (IMD), such as a pulse generator, electrically connected to the heart by at least one implantable defibrillator lead. More specifically, an implantable defibrillator lead provides an electrical pathway between the IMD, connected to a proximal end of the lead, and cardiac tissue, in contact with a distal end of the lead. In such a manner, electrical stimulation (e.g., in the form of one or more shocks or countershocks) emitted by the IMD may travel through the implantable defibrillator lead and stimulate the heart via one or more exposed, helically wound shocking coil electrodes located at or near the lead distal end portion. Once implanted, the exposed shocking coil electrodes often become entangled with fibrosis (i.e., a capsule of inactive tissue which grows into the exposed coils) with the end result being that a chronically implanted lead can be extremely difficult to remove by the application of tensile force to the lead proximal end.

Over time, situations may arise which require the removal and replacement of an implanted defibrillator lead. As one example, an implanted defibrillator lead may need to be replaced when it has failed, or if a new type of cardiac device is being implanted which requires a different type of lead system. As another example, bodily infection or shocking coil electrode dislodgement may require the replacement of an implanted defibrillator lead. In such situations, the implanted defibrillator lead may be removed and replaced with one or more different implantable leads.

To allow for easier removal, some implantable defibrillator leads include a fibrosis-limiting material covering a portion of the one or more otherwise exposed shocking coil electrodes thereon. When subjected to shear loads, such as during lead implantation procedures, the fibrosis-limiting material may separate from the associated shocking coil electrode or the shocking coil electrodes themselves may separate from the lead body or deform, thereby leaving uncovered coils that are subject to future fibrotic entanglement.

SUMMARY

Certain examples include a lead comprising a lead body, at least one shocking coil electrode, and a fibrosis-limiting material. The lead body extends from a lead proximal end portion to a lead distal end portion and may optionally include an inner insulating layer and an outer insulating layer. At least one shocking coil electrode is disposed along the lead body, for example, but not limited to, at one or both of the lead intermediate portion or the lead distal end portion. The shocking coil electrode includes one or more laser welded portions. The fibrosis-limiting material coaxially surrounds, at least in part, the at least one shocking coil electrode.

In another example, a lead assembly includes a lead body including elongate tubing extending from a first end portion to a second end portion and having an intermediate portion therebetween, and at least one electrode coil disposed along the lead body, the at least one electrode coil defined in part by a longitudinal axis and an electrode coil length. The electrode coil has end portions and an intermediate portion between the end portions. The lead assembly further includes at least one fibrosis limiting coating including one or more end portions, the one or more end portions disposed along an exterior portion of the at least one electrode coil, and the fibrosis limiting coating having a length longer than the electrode coil length.

In a further example, a method of manufacturing the lead includes forming a lead assembly including coating an external portion of at least one electrode coil with a coating of fibrosis limiting material, where the coating of fibrosis limiting material extends past end portions of the electrode coil. The method further includes disposing the electrode coil over an electrode coil fitting and anchoring the fibrosis limiting material between the electrode coil and the electrode coil fitting, coupling the at least one electrode coil with at least one conductor, and disposing insulative lead body over at least a portion of the at least one conductor and adjacent to the electrode coil and coating.

These and other examples, advantages, and features of the present leads and methods will be set forth in part in the detailed description, which follows, and in part will become apparent to those skilled in the art by reference to the following description of the present leads, methods, and drawings or by practice of the same.

BRIEF DESCRIPTION OF THE DRAWINGS

In the drawings, like numerals describe substantially similar components throughout the several views. Like numerals having different letter suffixes represent different instances of similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the present leads and methods may be practiced. These embodiments, which are also referred to herein as "examples," are described in enough detail to enable those skilled in the art to practice the present leads and methods. The embodiments may be combined, other embodiments may be utilized or structural or logical changes may be made without departing from the scope of the present leads and methods. The following detailed description is, therefore, not to be taken in a limiting sense, and the scope of the present leads and methods is defined by the appended claims and their legal equivalents.

In this document, the terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation.

Figure 1:
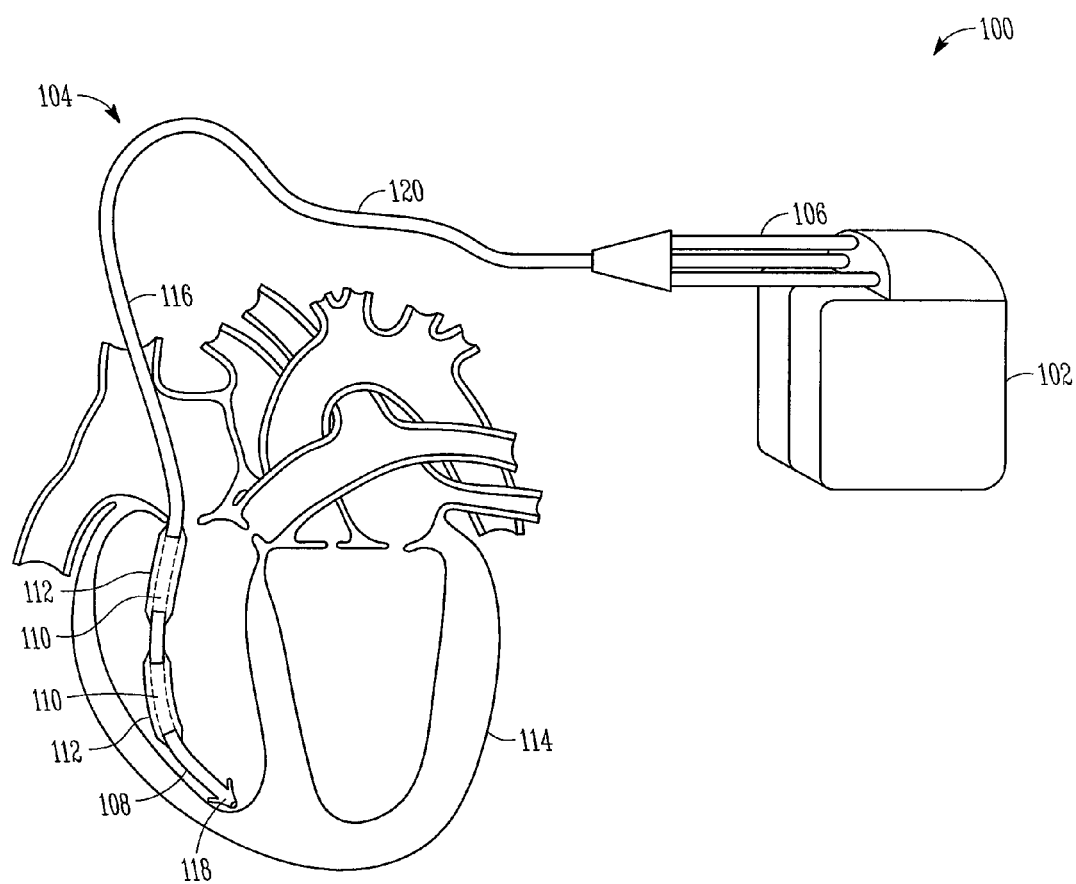
FIG. 1 illustrates a schematic view of a cardiac defibrillator system, including an implantable medical device and an implantable defibrillator lead, as constructed in accordance with at least one embodiment.

FIG. 1 illustrates a schematic view of a cardiac defibrillator system 100, which is useful for the correction of tachycardia or fibrillation, among other things. The system 100 includes an implantable medical device 102 and at least one implantable defibrillator lead 104. As shown, the implantable defibrillator lead 104 includes a lead body 120 extending from a lead proximal end portion 106, coupled with the implantable medical device 102, to a lead distal end portion 108 implanted within, on, or near a heart 114, with a lead intermediate portion 116 therebetween. The lead intermediate portion 116 or the lead distal end portion 108 includes at least one shocking coil electrode 110, wherein the at least one shocking coil electrode 110 is defined in part by a longitudinal axis and an electrode coil length. In this example, the at least one shocking coil electrode 110 is at least partially surrounded by a fibrosis-limiting material 112. In another embodiment, the fibrosis limiting material is disposed on areas where the shocking electrode 110 contacts or interacts with tissue or bodily fluids. In various examples, the fibrosis-limiting material 112 comprises a thin, polymeric layer coaxially surrounding and contacting an outer surface 370 (FIG. 3) of the helically wound shocking coil electrode 110.

The implantable defibrillator lead 104 transmits electrical signals between a selected location within, on, or about the heart 114 and the implantable medical device 102, such as to monitor the heart's 114 electrical activity at the selected location or to carry stimulation signals (e.g., one or more shocks or countershocks) to the selected location from the implantable medical device 102. The implantable defibrillator lead 104 may include a fixation assembly, such as one or more tines 118, or a helical coil, to anchor the lead distal end portion 118 at the selected location. The one or more tines 118 may be formed as part of the lead body 120, and thus may include a biocompatible lead body material, such as silicone rubber, polyurethane, polyimide, or a non-porous fluoropolymer. The fixation can be an active fixation assembly and/or a passive fixation assembly.

Figure 2:
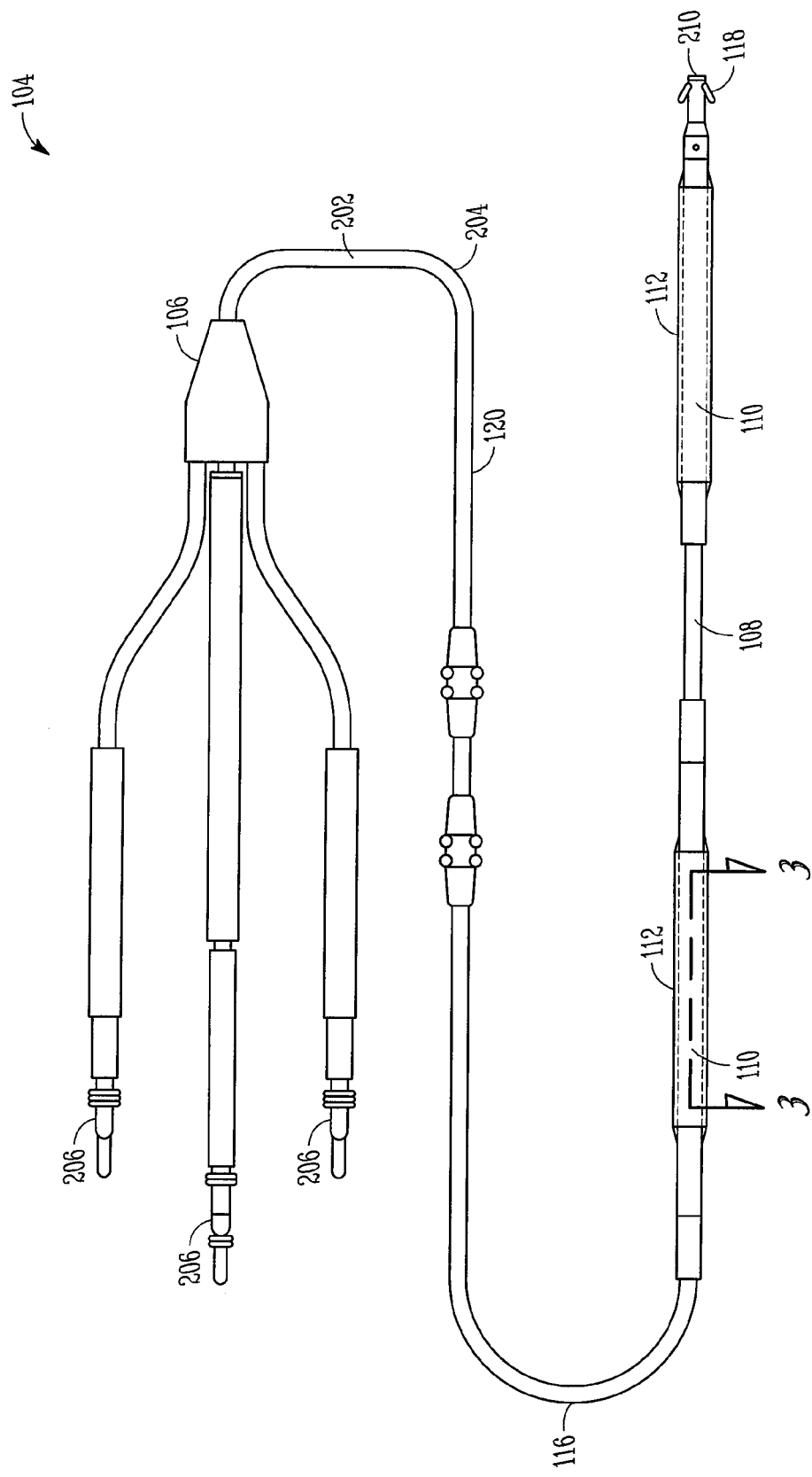
FIG. 2 illustrates a plan view of an implantable defibrillator lead, as constructed in accordance with at least one embodiment.

FIG. 2 illustrates a plan view of an implantable defibrillator lead 104, in an option. The implantable defibrillator lead 104 includes a lead body 120 extending from a lead proximal end portion 106 to a lead distal end portion 108 and having a lead intermediate portion 116 therebetween. In various examples, the lead body 120 includes an inner insulator layer 202, such as silicone rubber or other layer of impermeable polymeric electrically insulating material, and/or an outer insulator layer 204, such as polyurethane which provides high abrasion resistance.

In this example, the lead intermediate portion 116 and the lead distal end portion 108 include one or more shocking coil electrodes, such as a first and a second shocking coil electrode 110. The first and second shocking coil electrodes 110 include an uninsulated, helically wound shocking coil formed of a non-corrosive, bio-compatible metal, such as platinum, titanium, or alloys (e.g., platinum/iridium). The shocking coil electrodes 110 are covered by a pliable fibrosis-limiting material 112 (e.g., polytetrafluoroethylene (PTFE) or expanded PTFE (ePTFE)) in direct contact with an outer surface 370 (FIG. 3) of the shocking coil electrode 110. In an option, the fibrosis limiting material 112 is not entirely in direct contact with the coil electrode 110. The implantable defibrillator lead 104 of this example further comprises an optional distal tip electrode 210. The distal tip electrode 210 may be porous and include a metallic mesh. One or more conductors in the lead body 120 electrically and mechanically couple the electrodes 110, 210 to the lead proximal end portion 106. The conductors may be of any structure or combination of structures, such as coaxial or coradial coils separated by an insulating tube, or side-by-side cables or coils separated by a polymer, such as fluoropolymer, silicone, polyimide, or polyurethane.

In an option, the lead proximal end portion 106 includes one or more terminal leg connections 206 which are sized and shaped to couple to respective connector cavities incorporated into a header of the implantable medical device 102 (FIG. 1). It is through the coupling between the lead proximal end portion 206 and the connector cavities that the electrodes 110, 210 are electrically coupled to electronic circuitry within the implantable medical device 102. While FIG. 2 illustrates an implantable defibrillator lead 104 having three terminal connections 206 and three electrodes 110, 210, the present leads may vary, such as by including more or less than three terminal connections 206 and electrodes 110, 210.

Figure 3:
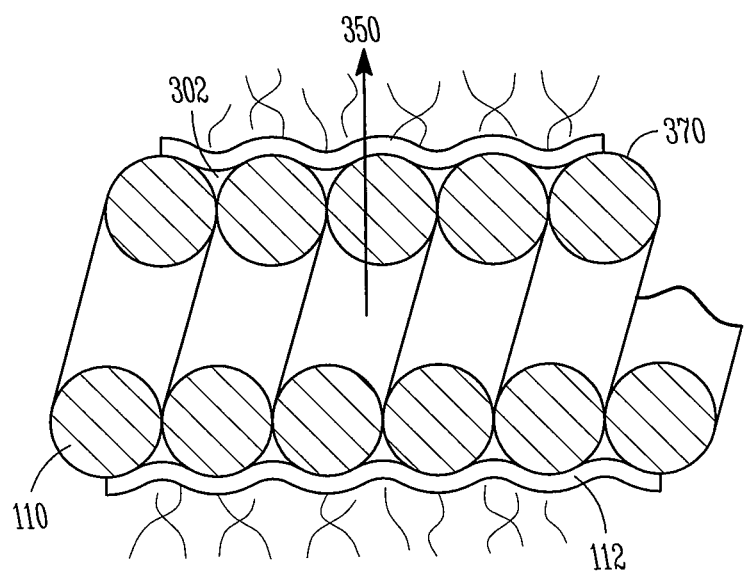
FIG. 3 illustrates an enlarged cross-sectional view of a portion of an implantable defibrillator lead, such as along line 3-3 of FIG. 2, and an implanted environment, as constructed in accordance with at least one embodiment.

FIG. 3 illustrates an enlarged cross-sectional view, such as along line 3-3 of FIG. 2, of a shocking coil electrode 110 surrounded by a thin, fibrosis-limiting material 112. As shown in this example, the fibrosis-limiting material 112 may be drawn into the coil gaps 302, such as via a heat sintering process, thereby eliminating or reducing the air volume present in the gaps. This tight conformation between the fibrosis-limiting material 112 and the shocking coil electrode 110 results in good electrical energy transmission 350 from the coil 110 to surrounding cardiac tissue. The use of the fibrosis-limiting material 112 as the tissue contacting portion of the shocking coil electrode 110 assists in preventing fibrotic tissue ingrowth.

Options for the fibrosis-limiting material 112 are as follows. For instance, the fibrosis-limiting material 112 may include PTFE, ePTFE, or other non-biodegradable and biocompatible materials, such as expanded ultra-high molecular weight polyethylene (eUHMWPE); may either be porous or non-porous; or may be inherently conductive or rely on porosity in conjunction with bodily fluids to be conductive. In various porous examples, the pore size is adequately small to allow penetration of conductive bodily fluids while substantially precluding tissue ingrowth, thus allowing a less traumatic removal of the defibrillator lead 104 after implantation should extraction become necessary. In various other examples, electrical conductivity through the fibrosis-limiting material 112 is not based on porosity, but rather is inherent in the material 112. For example, the fibrosis limiting material 112 is such that it can transfer electrical energy from the surface of the underlying electrode coil to the cardiac tissue it is in contact with. At least a portion of the outer surface of this material 112 is adapted to stimulate cardiac tissue, by being inherently electrically conductive, without relying on porosity and body fluid for charge transfer. The material 112 serves as the substrate for providing an electrically conductive path by way of either any suitable electrically conductive coatings deposited on the polymer surface, or any suitable electrically conductive particles blended with the polymer, prior to converting it to the final form. Examples of the substrate polymers include but are not limited to silicone rubber, polyurethane, and homopolymers or copolymers of polyolefin, fluoropolymer, polyamide and polyester. Examples of electrically conductive coatings on these polymers include but are not limited to coatings based on platinum, palladium, iridium, cobalt, silver, nickel and combinations thereof. Such coatings may be deposited by any methods commonly used in the industry, such as electrodeless deposition, plasma deposition, sputtering or chemical vapor deposition. In a further example, the fibrosis-limiting material 112 is wrapped around the coil electrode, for example, out of one or more strands of material.

Turning now to FIGS. 4A-4E, various techniques for manufacturing a lead having fibrosis-limiting material 112 are disclosed. These figures illustrate a side view of a portion of an implantable defibrillator lead 104, such as a shocking coil electrode 110, and a fibrosis-limiting material 112.

Figure 4A:
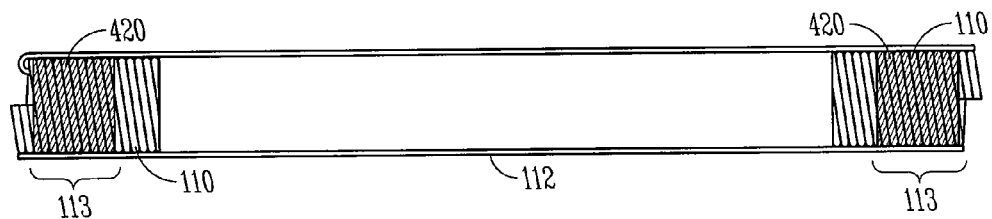
FIGS. 4A-4E illustrate a side view of a portion of an implantable defibrillator lead, as constructed in accordance with various embodiments.
Figure 4B:
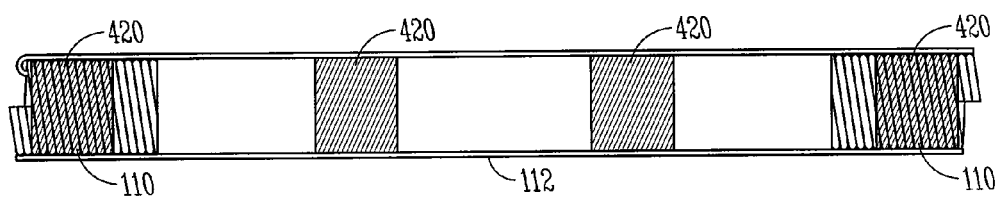
Figure 4C:
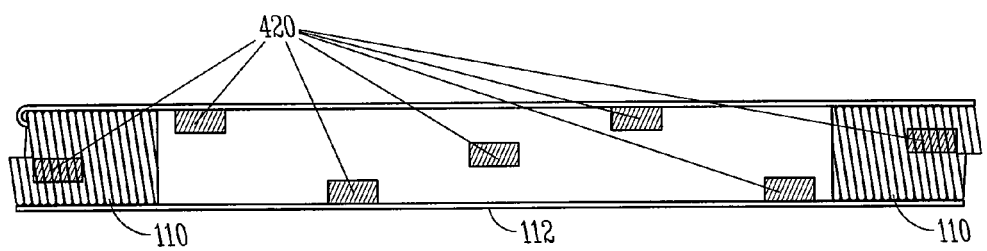

In an option, the shocking coil electrode 110 includes at least one laser weld portion 420. The at least one laser weld portion 420 is formed, for example, by laser welding the shocking coil electrode 110, for example, with a laser band that extends 360 degrees around the shocking coil electrode 110. In another option, the laser band only extends around a portion of the coil electrode 110. In an option, the at least one laser weld portion 420 is included at one or more end portions 113 of the shocking coil electrode 110. In a further option, the laser weld portion is formed on one or more filars of the shocking coil electrode 110. For example, the laser weld portion is formed, in an option, two or more filars of the shocking coil electrode 110, and in another option on 8-12 filars of the shocking coil electrode 110. In another option, about 5 mm of the shocking coil electrode 110 is formed inflexible, for example with the laser weld. In a further option, the filars are close wound coils. In a further option, multiple portions of the shocking coil electrode 110 can include laser weld portions 420, such as shown in FIGS. 4A, 4B, and 4C. For instance, the laser weld portions 420 can be helically disposed about the coil 110, and/or multiple discrete portions can be disposed about the coil 110.

In an option, end portions of the shocking coil electrode 110 include the laser weld, and additional discrete portions include the laser weld portion 420. The laser weld portions 420 can extend partially around the shocking coil electrode 110, or can extend 360 degrees around the shocking coil electrode 110. In a further option, for instance as shown in FIG. 4C, multiple discrete laser weld portions 420 can be included in a pattern along the shocking coil electrode 110, or can be randomly disposed along the shocking coil electrode 110.

The fibrosis-limiting material 112 coaxially covers the shocking coil electrode 110 and the laser weld portions 420 in a tightly conforming manner, in an option, and the laser weld portion 420 improves adhesive of the fibrosis limiting material 112 to the shocking coil electrode 110. For instance, the laser weld creates a relatively smooth surface for the fibrosis limiting material to attach to. In an option, the fibrosis-limiting material 112 extends to the ends of the shocking coil electrode 110. In a further option, the fibrosis limiting material 112 extends to less than a length of the shocking coil electrode 110.

In yet another option, the fibrosis limiting material 112 has a length that is greater than a length of the shocking coil electrode 110. For instance, one or more end portions 115 of the fibrosis limiting material 112 is able to cover the shocking coil electrode 110 and extend past the end portion 113 of the shocking coil electrode 110. This allows for the fibrosis limiting material 112 to be wrapped around end portions 113 of the shocking coil electrode 110, as further discussed below. In another option, a portion of the fibrosis limiting material 112 includes an opening 109 which overlaps, or is disposed over at least a portion of the shocking coil electrode 110. The opening 109 allows for access to the shocking coil electrode 110, without giving up the advantages of having the fibrosis limiting material 112 disposed on the shocking coil electrode 110.

In an option, the opening 109 has a shape such as, but not limited to, oval, circular or semicircular shape. In a further option, the opening 109 allows for a laser to access the shocking coil electrode 110, and allows for a weld to be made on the shocking coil electrode 110, while the fibrosis limiting material 112 is disposed on, over, or adjacent to the shocking coil electrode 110. The opening 109 can be formed by stamping, burning, cutting etc., and/or one or more openings can be formed in the fibrosis limiting material 112. In a further option, the fibrosis limiting material 112 has one or more slits 119 formed in one or more end portions 115. The slits can be formed with or without the opening 109. In an option, the slit extends from the end of the material 112 to a portion near the transition where the electrode 110 and the material 112 has a smaller diameter, as illustrated in FIG. 4E. The one or more slits 119 allow for the fibrosis limiting material 112 for forming of tethers on the material 112, which allows for the material 112 to be wrapped around the coil 110. Having the slit extend along the coil 110 also allows for laser banding of the coil.

Figure 4D:
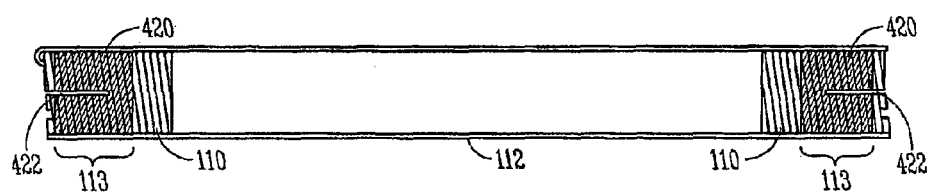
Figure 4E:
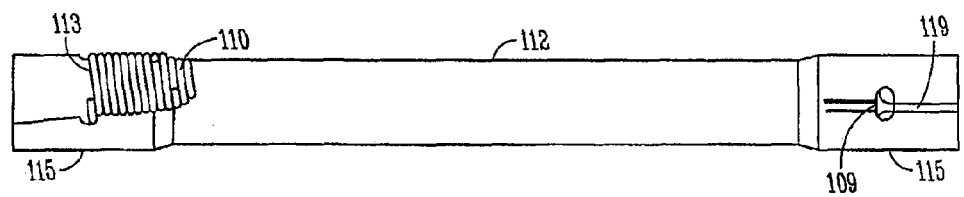

In a further option as shown in FIG. 4D, a laser weld portion 420 is at one more end portions 113 of the shocking coil electrode 110, and in an option is at each of the end portions 113 of the shocking coil electrode 110. The laser weld portion 420 includes at least one slit 422 therein, and in an option the at least one slit 422 is provided at each of the end portions 113. In an option, the at least one slit 422 includes two slits formed, for example, on opposite sides of the shocking coil electrode 110. The slit 422 allows for the shocking coil electrode 110 and/or the laser weld portion 420 to radially expand, for example, by 0.005-0.010 inches. For instance, the end portions 113 of the shocking coil electrode 110 have a larger inner diameter than an intermediate portion of the shocking coil electrode 110.

Figure 5A:
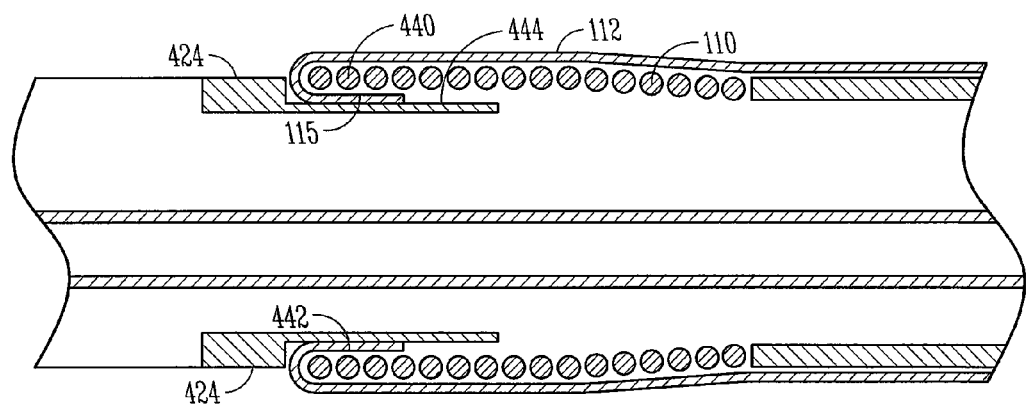
FIG. 5A illustrates a cross-sectional view of a portion of a lead, as constructed in accordance with at least one embodiment.

Referring to FIGS. 4D and 5A, the fibrosis-limiting material 112 is disposed over the laser band portion 420 and the shocking coil electrode 110 after the at least one slit 422 is formed in the laser band portion 420. The shocking coil electrode 110 can be expanded to fit over a fitting 424 via the at least one slit 422, and the expanded shocking coil electrode 110 puts radial tension in the fibrosis-limiting material 112, such as ePTFE, and increases resistance of movement of the fibrosis-limiting material 112 relative to the shocking coil electrode 110, and/or increases the adhesion between the fibrosis limiting material and the shocking coil electrode 110.

FIGS. 7A-7D illustrate various views of the fitting and illustrate the fitting 424 in greater detail. In an option, the fitting 424 generally has a cylindrical shape and is sized to be positioned within the shocking coil electrode 110 (FIG. 5A), and is defined in part by an exterior surface 444. In an option, the fitting 424 includes a projection 446 extending outwardly from the exterior surface 444, such as an annular projection that extends around a perimeter of the fitting 424. The projection 446, in a further option, can have other shapes or does not necessarily extend entirely around the perimeter of the fitting 424.

In a further option, the fitting 424 includes at least one through hole 448 therealong, or multiple through holes 448. For instance, two or more through hoes 448 are disposed on either side of the projection 446. In a further option, three or more through holes 448, or four through holes 448 are included. The through hole 448 allows for tubing external to the fitting 424, for instance tubing disposed on exterior surface 444, to contact tubing disposed internal to the fitting. In yet another option, the coil electrode fitting 424 includes conductor attachment features. For instance, in an option, the conductor attachment features includes at least one lumen 450 (FIG. 7D) where the conductor can be disposed and attached therein.

Figure 5B:
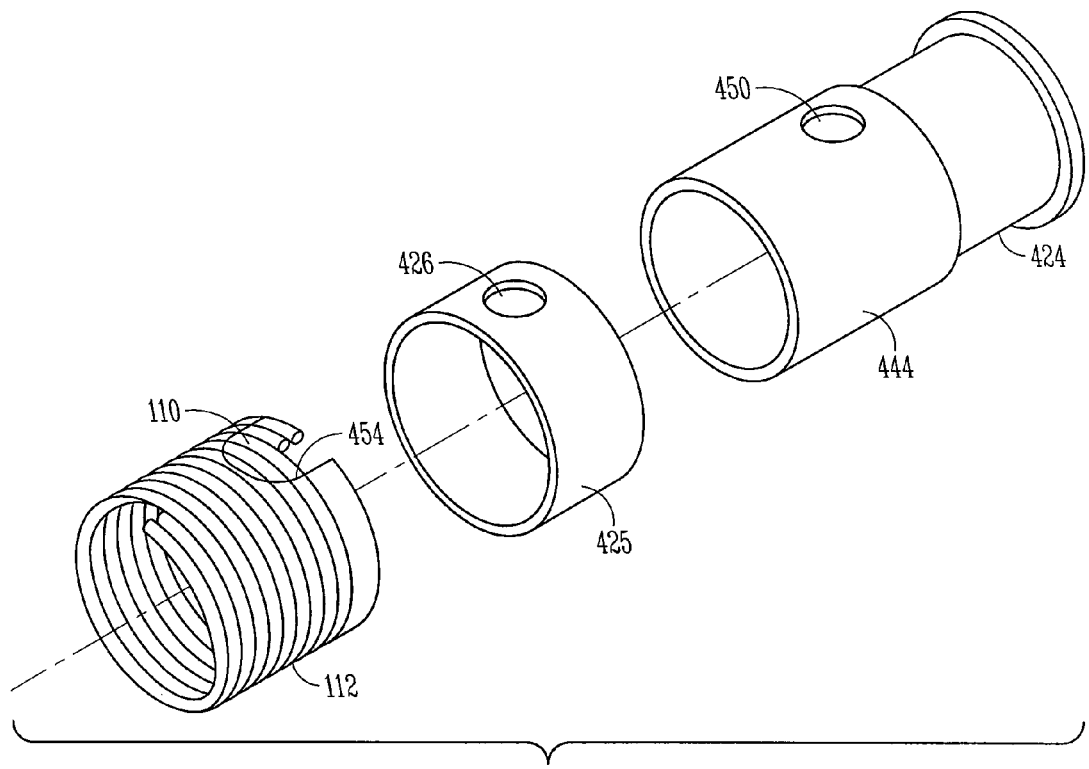
FIG. 5B illustrates an exploded isometric view of a portion of a lead, as constructed in accordance with at least one embodiment.
Figure 5C:
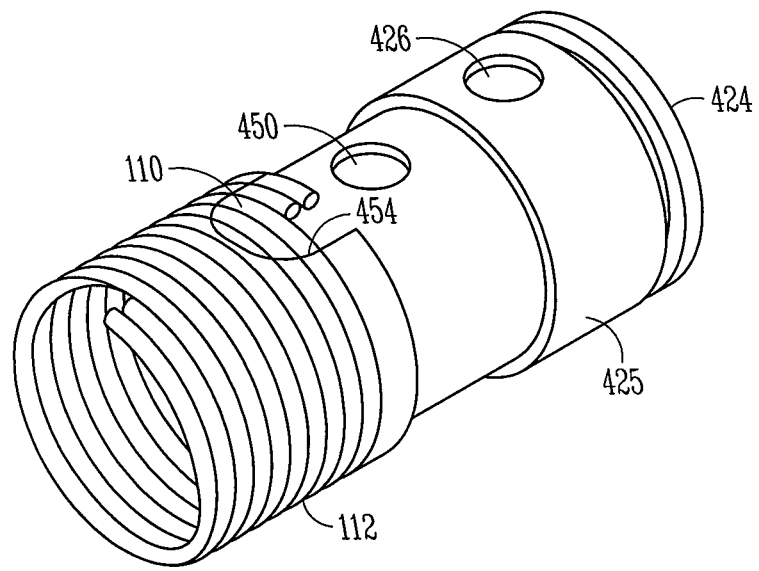
FIG. 5C illustrates an isometric view of a portion of a lead, as constructed in accordance with at least one embodiment.
Figure 5D:
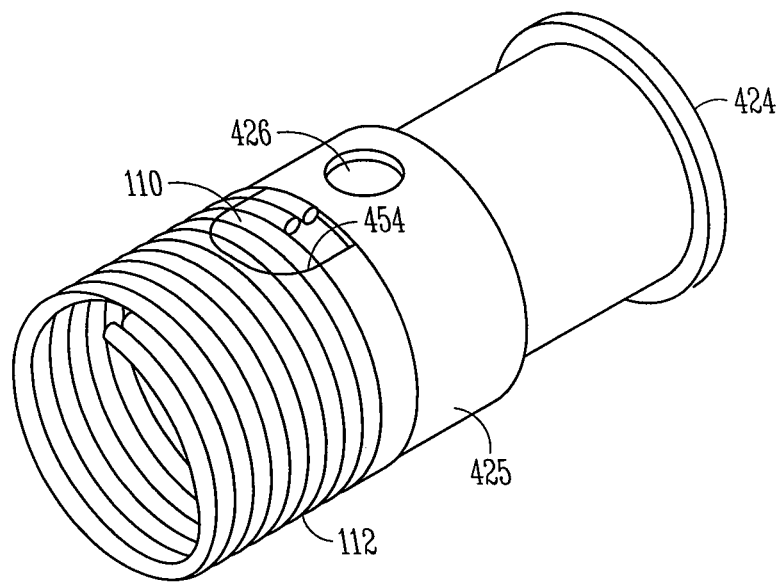
FIG. 5D illustrates an isometric view of a portion of a lead, as constructed in accordance with at least one embodiment.

FIGS. 5A-5G illustrate various options for manufacturing the lead which include the fibrosis limiting material 112 includes one or more end portions 115 that extend around end portions 440 of the shocking coil electrode 110, allowing for the fibrosis limiting material 112 to be anchored between the fitting 424 and the electrode coil 110. FIGS. 5B-5D illustrate an assembly including a coil fitting 424, a coated electrode 110, and a ring 425. The ring 425 includes an opening 426, and the ring is placed on the fitting 424. The coil fitting 424 receives the coated coil electrode 110 an external surface 444 thereof. Portions 115 of the fibrosis limiting material 112 are disposed between an interior surface 442 of the coil and an exterior surface 444 of the fitting 424, as can be seen in FIG. 5A. In yet another option, the fibrosis limiting material 112 includes an opening such as a cut out 454, where material is removed from the coating of fibrosis limiting material 112 so that the electrode coil 110 can be welded in the cut out 454. The ring 425, in an option, is slid toward the coil 110 and the opening 426 is substantially aligned with the opening 450.

Figure 5E:
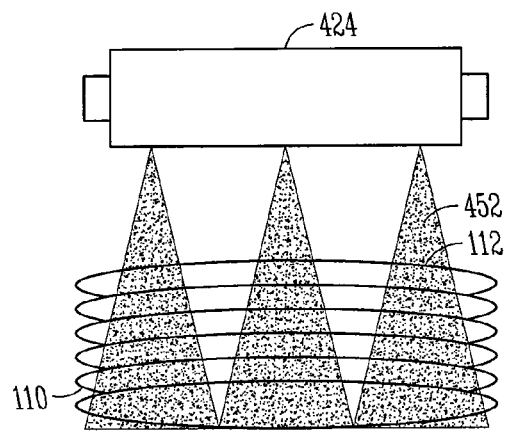
FIG. 5E illustrates a schematic view of a portion of a lead, as constructed in accordance with at least one embodiment.
Figure 5F:
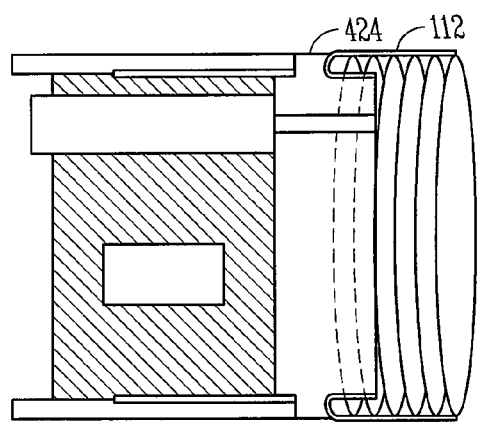
FIG. 5F illustrates a schematic view of a portion of a lead, as constructed in accordance with at least one embodiment.
Figure 5G:
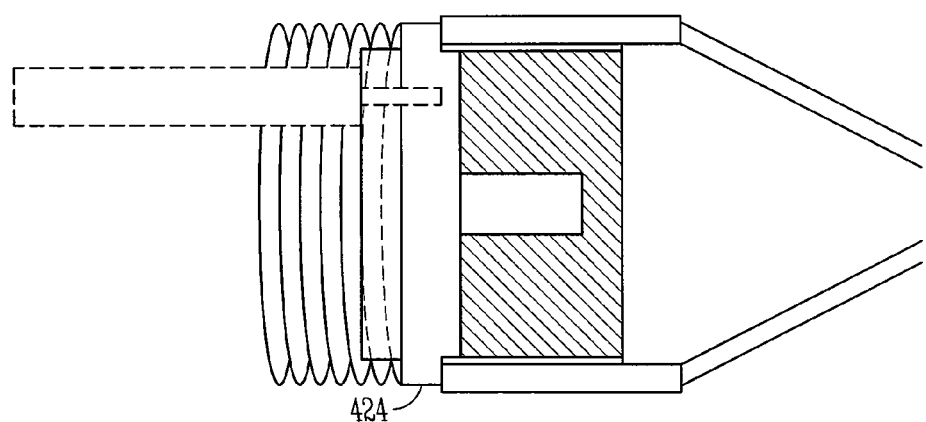
FIG. 5G illustrates a schematic view of a portion of a lead, as constructed in accordance with at least one embodiment.

In a further option, the fibrosis limiting material 112, in an option, includes one or more tethers 452, as shown in FIGS. 5E-5G. The tethers 452 are formed by cutting portions 115 of the fibrosis limiting material 112, where the portions 115 allow for the fibrosis limiting material 112 to extend to a length longer than the coil electrode 110, which allows for the tethers to be disposed between the exterior surface of the fitting 424 and an interior portion 442 of the electrode coil 110, as shown in FIG. 5F. In an option, two or more tethers 452 are formed on each end portion of the fibrosis limiting material 112, or in a further option three or more tethers 452 are formed on each end portion of the fibrosis limiting material. In an option, the tethers 452 are tapered from a relatively wide portion to a narrower portion, as shown in FIG. 5E. In another option, the tethers 452 have substantially uniform width. The tethers can be formed by slitting the material, for example as shown in FIG. 4E. In a further option, the coil electrode 110 includes a corresponding number of welded portions to the number of tethers.

In yet another option, the electrode coil 110 can be coated with fibrosis limiting material 112. Portions of the electrode coil 110 can be removed, for example, by peeling back the coating and cutting the coil to create a coil 110 having a shorter length than a length of the coating of fibrosis limiting material 112. This allows for the fibrosis limiting material 112 to be wrapped around end portions of the electrode coil 110 as discussed above and below. In a further option, the electrode coil 110 includes end portions which have an expanded outer diameter relative to an intermediate portion of the electrode coil 110, as shown in FIG. 4E. The fibrosis limiting material 112 conforms o the expanded coil 110.

Figure 6:
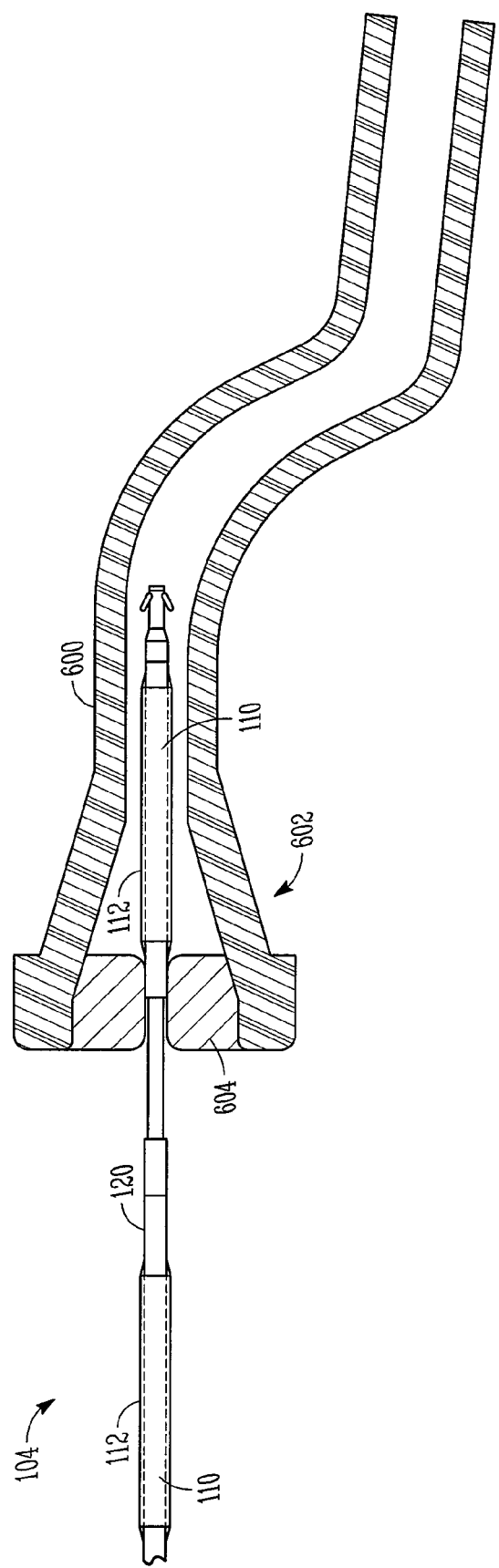
FIG. 6 illustrates a schematic view of an implantable defibrillator lead being advanced through an introducer sheath (shown in cross-section), as constructed in accordance with at least one embodiment.
Figure 7A:
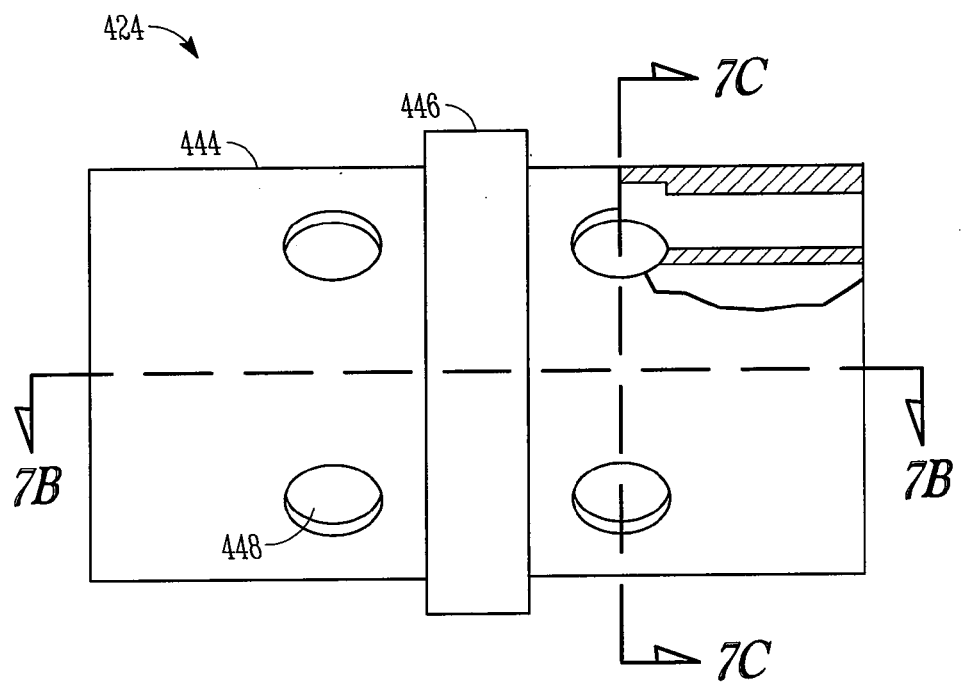
FIG. 7A illustrates a side view of a fitting, as constructed in accordance with at least one embodiment.
Figure 7B:
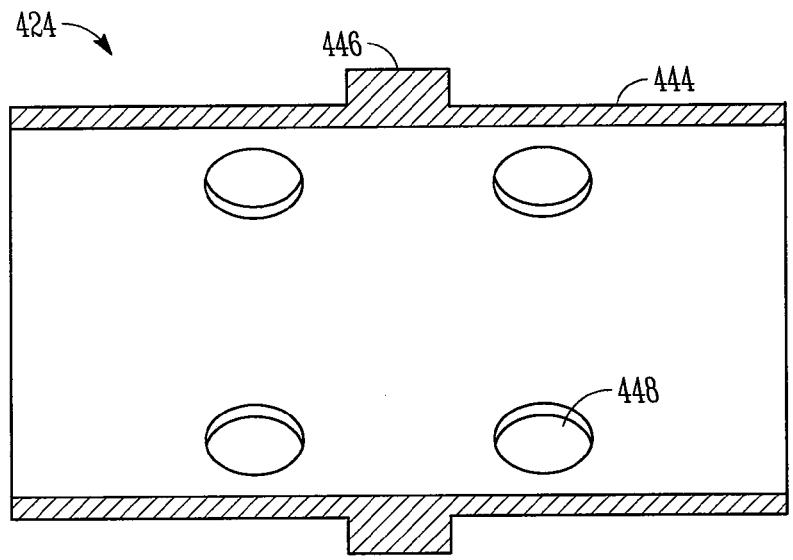
FIG. 7B illustrates a cross-sectional view of a fitting taken along 7B-7B of FIG. 7A.
Figure 7C:
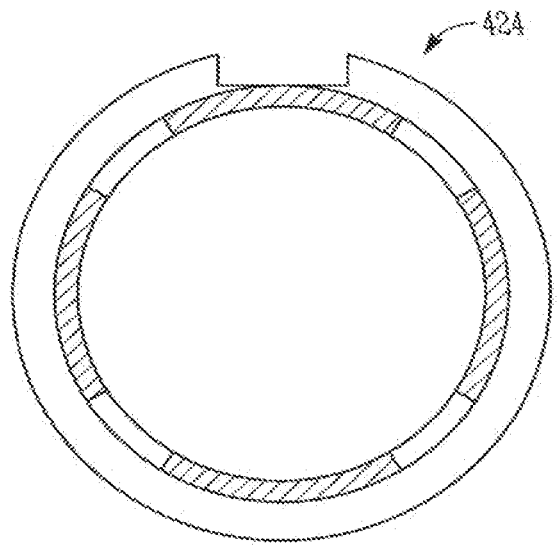
FIG. 7C illustrates a cross-sectional view of a fitting taken along 7C-7C of FIG. 7A.
Figure 7D:
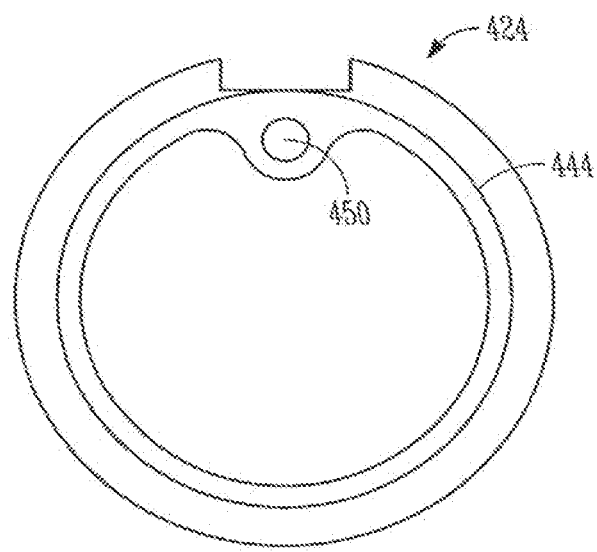
FIG. 7D illustrates an end view of a fitting, as constructed in accordance with at least one embodiment.

Implantable defibrillator leads 104 are placed in contact with cardiac tissue by passage through a venous access, such as the subclavian vein, the cephalic vein, or one of its tributaries. In such a manner, an implantable defibrillator lead 104 may advantageously be placed in contact with the heart 114 (FIG. 1) without requiring major thoracic surgery. Instead, an implantable defibrillator lead 104 may be introduced into a vein and maneuvered therefrom into contact with the heart 114 or tissue thereof. A multi-step procedure is often required to introduce implantable defibrillator leads 104 within the venous system. Generally, this procedure consists of inserting a hollow needle into a blood vessel, such as the subclavian vein. A guide wire is then passed through the needle into the interior portion of the vessel and the needle is withdrawn. As illustrated in FIG. 6, an introducer sheath 600 with a dilator assembly 602 may be inserted over the guide wire into the vessel for lead 104 introduction. The sheath 600 is advanced to a suitable position within the vessel, such that a distal end thereof is well within the vessel, while a proximal end thereof is outside the patient.

When a physician implants a defibrillator lead 104, such as through the introducer sheath 600 and specifically an introducer seal 604, high drag forces may be created along the lead body 120. As a result of these high drag forces, previous lead component interfaces including the fibrosis-limiting material 112 to shocking coil electrode 110 and the shocking coil electrode 110 to the lead body 120 could separate or shift relative to one another leaving uncovered coil portions subjected to future fibrotic entanglement (e.g., the shocking coil electrode 110 became stretched, which in turn pulled the fibrosis-limiting material 112 away from the coil 110 and exposed a portion of the coil to fibrotic growth). Using the present lead manufacturing technologies, it has been found that such separating or shifting between the fibrosis-limiting material 112, the shocking coil electrode 110, and the lead body 120 is reduced or eliminated, thereby preventing fibrotic entanglement and facilitating lead extraction should it become necessary. The electrode coil 110 and the fibrosis-limiting material 112 of the lead 104 can withstand a drag force of about 0.5 to 1.0 pounds.

A method of manufacturing an implantable defibrillator lead including robust attachment between a fibrosis-limiting material, a shocking coil electrode, and a lead body is described herein. The lead assembly is formed including coating an external portion of at least one electrode coil with a coating of fibrosis limiting material, where the coating of fibrosis limiting material extends past end portions of the electrode coil. The fibrosis-limiting material is formed onto an outer surface of the at least one shocking coil electrode, such as through the use of heat. Further methods for manufacturing the fibrosis-limiting material and/or applying the fibrosis-limiting material to the electrode can be used. In an example, the fibrosis limiting material 112 includes PTFE nonwoven web. In an example, to manufacture the PTFE nonwoven web, a PTFE powder is made into a paste, and molded. In another example, the porous thin film covering includes a thin, high strength, stretched, non-woven web of polytetrafluoroethylene which is composed of nodes interconnected by fibrils. In another option, the fibrosis limiting material 112 is applied using a wrapping process, such as with a film wrapping machine. Various options can be used as the film is wrapped. For instance, the film can be wrapped at a certain angle, or a number of passes can occur. After the wrapping process, the assembly of the coil electrode and the fibrosis limiting material 112 can be heated, resulting in the film layers adhering together, and the material 112 is contracted on to the coil electrode 110.

Optionally, the method further includes laser welding at least a portion of at least one electrode coil, for example, but not limited to at one or more ends of the coil, and/or at one or more discrete locations of the coil, and/or helically along the coil, and/or around 360 degrees around the coil. The laser welding can be done in the various embodiments discussed above, and/or illustrated in the drawings. In a further option, one or more slits are formed in the laser welded portions, such as at one or each of the end portions of the coil, for example with two slits. The laser welding can occur prior to coating the electrode coil.

In a further option, the electrode coil is disposed over an electrode coil fitting, where the fitting is within the electrode coil, and the fibrosis limiting material is anchored between the electrode coil and the electrode coil fitting. For instance, end portions of the coating of fibrosis limiting material are disposed within the electrode coil. In a further option, a portion of the fibrosis limiting material is removed so that the electrode can be welded to the fitting. In yet another option, at least one through hole is formed through the fitting, and optionally tubing on an external portion of the fitting can make contact, such as adhesive contact, with tubing in the fitting, such as a multi lumen tubing. In yet another option, one or more tethers are formed in the fibrosis limiting material and are tucked between an exterior surface of the electrode fitting and an interior portion of the at least one electrode coil. At least one conductor is electrically coupled with the electrode coil. One or more portions, such as end portions, of the at least one shocking coil electrode are coupled to a lead body or component. Optionally, the coupling between the shocking coil electrode and the lead body includes the use of an adhesive.

It is to be understood that the above description is intended to be illustrative, and not restrictive. For instance, any of the aforementioned examples may be used individually or with any of the other examples. In addition, the aforementioned examples may or may not include the use of adhesives (e.g., medical adhesives) for selected component attachment. Many other embodiments may be apparent to those of skill in the art upon reviewing the above description. The scope of the present leads and methods should, therefore, be determined with reference to the appended claims, along with the full scope of legal equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, assembly, article, or process that includes elements in addition to those listed after such a term in a claim are still deemed to fall within the scope of such claim.

The Abstract of the Disclosure is provided to comply with 37° C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A lead assembly comprising:
   a lead body including elongate tubing extending from a first end portion to a second end portion and having an intermediate portion therebetween;
   at least one electrode coil disposed along the lead body, the at least one electrode coil is defined in part by a longitudinal axis, a length, one or more end portions, a plurality of windings, and an interior portion;
   at least one coil electrode fitting defined in part by an exterior surface, at least a portion of the coil electrode fitting is disposed within a portion of the electrode coil;
   at least one fibrosis limiting coating having a length greater than the length of the at least one electrode coil and including one or more end portions, the fibrosis limiting coating being disposed along an exterior portion of the at least one electrode coil and extending past the one or more end portions of the at least one electrode coil, the fibrosis limiting coating wrapped around the one or more end portions of the at least one electrode coil and the one or more end portions of the fibrosis limiting coating being disposed between the exterior surface of the at least one coil electrode fitting and the interior portion of the at least one electrode coil, wherein no portion of the fibrosis limiting coating is disposed between windings of the at least one electrode coil.

2. The lead assembly as recited in claim 1, wherein the coil electrode fitting has at least one through hole disposed through the fitting.

3. The lead assembly as recited in claim 2, wherein tubing external to the coil electrode fitting contacts internal tubing through the at least one through hole.

4. The lead assembly as recited in claim 1, wherein the coil electrode fitting includes conductor attachment features.

5. The lead assembly as recited in claim 1, wherein the one or more end portions of the fibrosis limiting coating includes one or more tethers, and the one or more tethers are disposed between the exterior surface of the at least one coil electrode fitting and the interior portion of the at least one electrode coil.

6. A lead assembly comprising:
   a lead body including elongate tubing extending from a first end portion to a second end portion and having an intermediate portion therebetween;
   at least one electrode coil disposed along the lead body, the at least one electrode coil is defined in part by a longitudinal axis, an interior portion, a plurality of windings, and an electrode coil length, the electrode coil having end portions and an intermediate portion between the end portions;

at least one coil electrode fitting defined in part by an exterior surface, at least a portion of the coil electrode fitting is disposed within the interior portion of the at least one electrode coil; and at least one fibrosis limiting coating including one or more end portions, the one or more end portions disposed along an exterior portion of the at least one electrode coil, the fibrosis limiting coating having a length longer than the electrode coil length and wrapped around the end portions of the electrode coil and the one or more end portions of the fibrosis limiting coating being disposed between the exterior surface of the at least one coil electrode fitting and the interior portion of the at least one electrode coil, wherein no portion of the fibrosis limiting coating is disposed between windings of the at least one electrode coil.

7. The lead assembly as recited in claim 6, wherein the electrode coil end portions have a larger diameter than the intermediate portion.

8. The lead assembly as recited in claim 6, wherein the fibrosis limiting coating end portions include at least one opening therein.

9. The lead assembly as recited in claim 6, wherein the fibrosis limiting coating end portions include at least one slit therein.

10. The lead assembly as recited in claim 6, wherein the at least one electrode coil includes at least one weld portion.

11. The lead assembly as recited in claim 10, further comprising at least one slit in the at least one weld portion.

12. The lead assembly as recited in claim 11, wherein the at least one weld portion and the at least one slit is disposed at one end portion of the at least one electrode coil.

\* \* \* \* \*